United States Patent [19]

Tesch

[11] Patent Number: 5,263,479
[45] Date of Patent: Nov. 23, 1993

[54] PACKING FOR THERMOTHERAPY

[76] Inventor: Gunter Tesch, Avenue Jean-Marie-Musy 15, CH-1700 Fribourg, Switzerland

[21] Appl. No.: 659,337
[22] PCT Filed: Jul. 9, 1990
[86] PCT No.: PCT/EP90/01109
  § 371 Date: Apr. 16, 1991
  § 102(e) Date: Apr. 16, 1991
[87] PCT Pub. No.: WO91/00716
  PCT Pub. Date: Jan. 24, 1991

[30] Foreign Application Priority Data

Jul. 10, 1989 [CH] Switzerland .......... 02564/89

[51] Int. Cl.$^5$ .............................................. A61F 7/00
[52] U.S. Cl. ................................. 607/114; 62/530
[58] Field of Search ..................... 128/399–403, 128/374, 380; 62/530, 4; 428/85, 234, 288

[56] References Cited

U.S. PATENT DOCUMENTS

| | | | |
|---|---|---|---|
| 4,413,030 | 11/1983 | Tesch et al. | 428/85 |
| 4,481,247 | 11/1984 | Tesch et al. | 428/234 |
| 4,820,574 | 4/1989 | Tesch | 428/234 |
| 4,865,012 | 9/1989 | Kelley | 128/403 |
| 4,917,943 | 4/1990 | Tesch | 428/288 |

FOREIGN PATENT DOCUMENTS

| | | |
|---|---|---|
| 0013427 | 7/1980 | European Pat. Off. . |
| 0013428 | 7/1980 | European Pat. Off. . |
| 46896 | 3/1982 | European Pat. Off. . |
| 71211 | 2/1983 | European Pat. Off. . |
| 162583 | 11/1985 | European Pat. Off. . |
| 0257658 | 3/1988 | European Pat. Off. . |
| 276682 | 8/1988 | European Pat. Off. . |

Primary Examiner—Mark S. Graham
Attorney, Agent, or Firm—Bacon & Thomas

[57] ABSTRACT

The invention concerns a thermotherapeutic packing, in particular for cryotherapy, comprising an impermeably-welded packing casing consisting of a flexible sheet and a heat- or cold-storing liquid and in insert material of spherical bodies comprising aggregates of fibers wound into balls or spheres.

The liquid can penetrate these spherical aggregates and accordingly, the packing volume may be less. This packing not only is easily molded, but exhibits gradual heat loss or heat absorption.

7 Claims, No Drawings

PACKING FOR THERMOTHERAPY

The invention concerns a thermotherapeutic packing for medical use comprising a casing made of a flexible, impermeably welded sheet containing a heat- or cold-storing liquid and an insert material of spherical aggregates. The thermotherapeutic packing of this invention is used for treating various ailments and injuries necessitating the application of heat- or cold-packs to body areas.

BACKGROUND OF THE INVENTION

Illustratively, such a packing is known from the European patent document, A 0 046 894. The insert material of this packing consists of closed-pore foam particles in bulk which cannot fully absorb the heat-or cold-storing liquid. These foam particles are polystyrene spheres which, in this shape, are easily displaced relative to one another. They are 1 to 5 mm in diameter, especially 4 to 5 mm, and are temperature-insensitive. A packing filled with spheres allows excellent molding to specific body sites.

However, it has been found in practice that the need for molding capability precludes tautly filling the packing with spheres; thus, these spheres disclosed in EP A 0 046 894 can move so much within the packing casing that they may concentrate in one part of it whereas no plastic spheres are present in the other part of the pouch-shaped packing. In fact, this is desirable to the extent that the packing lies horizontally on a body part because then the foam particles will buoy at the side away from the body and form an insulating layer. However, when the packing is not applied horizontally, this buoyancy causes the foam particles to concentrate at one end of the packing and, as a result, undesirable, uneven thermal behavior is incurred over the area of the packing.

The displacement of the spheres into one part of the packing takes place when the packing is stored, not (surface) prone, but standing on one edge. Deliberate, thorough mixing of the packing contents is quite different.

Moreover, the foam spheres fill a large part of the packing volume. However, the spheres cannot store heat; that is, only the liquid assures heat storage, but this liquid takes up only somewhat than half the packing volume for a commercial packing made in the manner of the patent application. In order to absorb or dissipate as much heat as other packings, such a packing must be made about twice as thick.

The European patent document A 0 046 894 further describes a pouch-shaped packing which is assumed already known in that text, in which the insert material consists of an integral and essentially planar foam absorbing the liquid. Essentially, this foam serves to assure uniform thickness of the packing because the two sheets of the pouch-like packing rest on this foam over the entire packing area once the liquid has been substantially absorbed by the foam.

However, such packing is not easily molded, that is, matching to the body surface is limited. Also, temperature loss is unhampered and frequently high and rapid heat transfer takes place, i.e., the body part is excessively cooled or heated, such effects on one hand decaying too rapidly and on the other hand, they may entail undesired phenomena such as frostbites or burns.

SUMMARY OF THE INVENTION

The object of the invention is to create a thermotherapeutic packing for medical use of the above species which allows good molding and of which the heat loss or absorption shall be slower, i.e., shall take place over a longer time.

This problem is solved by a packing comprising a hermetically-sealed casing containing a heat-storage or cold-storage liquid and a filling comprising spherical bodies, wherein the spherical bodies are in the form of aggregates of fibers wound into spheres. The spherical bodies permit the cooling or heating medium to penetrate and flow through the aggregates.

For years such aggregates have been used in carpet-making (European patent documents A 0 013 427 and A 0 013 427) and, more recently, as down substitutes in the bedding industry (European patent documents A 0 257 658 and 0 276 682). Whereas the fiber aggregates used in bedding should evince a large restoring force following compression, which also would be advantageous in the present case, more compact aggregates are being used here.

Nevertheless, the aggregate fibers used in the thermotherapeutic packing of the present invention assume only a slight volume because the coolant or heating medium can penetrate and pass through the aggregates, whereby nearly the entire packing volume may be utilized for the coolant or heating medium.

On the other hand, the coolant or heating medium is hampered by the aggregates from assuming a convection flow, even though they do not exclude it. The thermal conductivity of the fibers should be as low as possible.

This packing design offers relatively slow heat dissipation or absorption, so that such packing can rest for a substantial time on the body being treated.

DESCRIPTION OF THE PREFERRED EMBODIMENTS

Advantageously, the aggregates comprise synthetic fibers inert relative to the medium, such as polypropylene fibers. The fibers can optionally be colored or dyes so that the user can spot them in the packing and assess the packing's received condition.

In a preferred embodiment mode, the spherical aggregates have fiber ends projecting from them. This assures that the aggregates cannot move relative to each other. Reference is made in this regard to the European patent document A 0 025 658, describing such special aggregates.

This feature also prevents the mixture of solid and liquid from shifting inside the packing when being molded onto the body because the aggregates ensure that the two sheets enclosing the liquid over the packing surface remain uniformly distant from each other.

The packing envelope is made of polyurethane. This material is stable in the required temperature range while nevertheless being easily molded to the body.

While the invention has been described in connection with one of its preferred embodiments, it should be understood that changes and modifications may be made without departing from the scope of the appended claims.

I claim:

1. A pack for thermotherapy comprising a liquid impermeable, welded flexible sheet pack casing containing particles of spherical fiber aggregates of entangled fibers which allow a heat- or cold-storing liquid to penetrate and flow through the fiber aggregates and a heat- or cold-storing liquid.

2. The pack defined in claim 1, wherein said fibers are synthetic.

3. The pack defined in claim 1, wherein the spherical aggregates have fiber ends projecting from them.

4. The pack defined in claim 1, wherein said fibers have a thermal conductivity that is substantially less than the thermal conductivity of the heat- or cold-storing liquid.

5. The pack defined in claim 1, wherein the pack envelope is made of polyurethane.

6. The pack defined in claim 1, wherein said fibers are colored or dyed.

7. The pack defined in claim 1, wherein said fibers are comprised of polypropylene.

* * * * *